(12) United States Patent
Justice et al.

(10) Patent No.: US 10,000,577 B2
(45) Date of Patent: Jun. 19, 2018

(54) TREATMENT OF OTITIS MEDIA (71) Applicant: Research Institute at Nationwide Children's Hospital, Columbus, OH (US)

(72) Inventors: Sheryl S. Justice, Westerville, OH (US); Kevin M. Mason, Blakclick, OH (US); Alistair Harrison, Westerville, OH (US)

(73) Assignee: Research Institute At Nationwide Children's Hospital, Columbus, OH (US)

( * ) Notice: Subject to any disclaimer, the term of this patent is extended or adjusted under 35 U.S.C. 154(b) by 0 days. days.

(21) Appl. No.: 15/510,942

(22) PCT Filed: Sep. 11, 2015

(86) PCT No.: PCT/US2015/049645
§ 371 (c)(1),
(2) Date: Mar. 13, 2017

(87) PCT Pub. No.: WO2016/040778
PCT Pub. Date: Mar. 17, 2016

(65) Prior Publication Data
US 2017/0275379 A1  Sep. 28, 2017

(51) Int. Cl.
| | |
|---|---|
| *C07K 16/42* | (2006.01) |
| *A61K 47/42* | (2017.01) |
| *A61K 39/02* | (2006.01) |
| *A61K 38/17* | (2006.01) |
| *A61K 38/16* | (2006.01) |
| *A61K 38/00* | (2006.01) |
| *A61K 47/00* | (2006.01) |
| *A61K 39/00* | (2006.01) |

(52) U.S. Cl.
CPC .......... *C07K 16/4233* (2013.01); *A61K 38/16* (2013.01); *A61K 38/17* (2013.01); *A61K 39/0208* (2013.01); *A61K 47/42* (2013.01); *A61K 38/00* (2013.01); *A61K 47/00* (2013.01); *A61K 2039/505* (2013.01)

(58) Field of Classification Search
CPC .... C07K 16/4233; A61K 38/16; A61K 38/17; A61K 39/0208; A61K 47/42; A61K 38/00; A61K 47/00; A61K 2039/505
USPC ........................................................ 514/2.3
See application file for complete search history.

(56) References Cited

U.S. PATENT DOCUMENTS

| 5,364,633 A | 11/1994 | Hill et al. |
| 5,500,416 A | 3/1996 | Miyazawa et al. |
| 7,192,702 B2 | 3/2007 | Zhan et al. |

FOREIGN PATENT DOCUMENTS

KR   2014056413 A   5/2014

OTHER PUBLICATIONS

Holmes, KA et al. "Adherence of Non-Typeable Haemophilus Influenzae Promotes Reorganization of the Actin Cytoskeleton in Human or Chinchilla Epithelial Cell in Vitro" Microbial Pathogenesis, 1997, vol. 23, No. 3, pp. 157-166; p. 161, second column, second paragraph; p. 162, first column, second-third paragraphs; p. 163, first column, third paragraph (10 pages).
Baggett, AW et al. "Structural Characterization and Computer-aided Optimization of a Small Molecule Inhibitor of Arp2/3 Complex, a Key Regulator of the Actin Cytoskeleton" ChemMedChem, 2012, vol. 7, No. 7, pp. 1286-1294 (pp 1-18); abstract; p. 2, first paragraph (18 pages).
Harmes, KM et al. "Otitis Media: Diagnosis and Treatment" American Family Physician, 2013, vol. 88, No. 7, pp. 435-440; abstract; p. 437, second column, third paragraph; p. 438, first column, first-third paragraphs; p. 439, first column, first-second paragraphs; tables 3, 5 (6 pages).
International Search Report and Written Opinion dated Dec. 10, 2015 (7 pages).
Auinger et al, "Trends in Otitis Media Among Children in the United States." Pediatrics, 2003, vol. 112, Issue 3, pp. 514-520.
Bauchner et al. "Reducing Inappropriate Oral Antibiotic Use: A Prescription for Change," Pediatrics, 1998, vol. 102, issue 1, pp. 142-145.
Holder et al, "Orie third of middle ear effusions from children undergoing tympanostomy tube placement had multiple bacterial pathogens," BMC Pediatrics, 2012, vol. 12:87, pp. 1-7.
Novotny et al. "Kinetic analysis and evaluation of the mechanisms involved in the resolution of experimental nontypeable *Haemophilus influenzae*-induced otitis media after transcutaneous immunization." Vaccine, 2013, vol. 31(34), pp. 3417-3426.
Harrison at al,"Ferric Uptake Regulator and Its Role in the Pathogenesis of Nontypeable *Haemophilus influenzae*." Infect Immun, 2013, vol. 81, No. 4, pp. 1221-4233.
Raffel et al, "The *Haemophilus influenzae*Sap Transporter Mediates Bacterium-Epithelial Cell Homeostasis." Infect Immun, 2013, vol. 81, No. 1, pp. 43-54.
Whitby et al. "Comparison of transcription of the *Haemophilus influenzae*Iron/heme modulo genes in vitro and in vivo in the chinchilla middle ear." BMC Genomics, 2013, vol. 14:925, pp. 1-12.
Mason et al, "Nontypesble *Haemophilus influenzae*Gene Expression Induced in Vivo in a Chincilla Model of Otitis Media." Infect Immun, 2003, vol. 71, No. 6, pp. 3454-3462.
Gorelik et al. "Arpin, a novel inhibitor of the ARP2/3 complex, controls cellular migration." Med Set (Paris), 2014, vol. 30(3), pp. 248-250. English explanation of relevance and translation.
Nolen et al, "Characterization of two classes of small molecule inhibitors of Arp2/3 complex." Nature, 2009, vol. 460(7258), pp. 1031-1034.

(Continued)

*Primary Examiner* — Kristin A Vajda
(74) *Attorney, Agent, or Firm* — Tarolli, Sundheim, Covell & Tummino LLP (57) ABSTRACT

A method of treating otitis media in a subject is described that includes administering to the subject a therapeutically effective amount of an Actin-Related Protein 2/3 Complex (Arp2/3) inhibitor. The role of Arp2/3 in otitis media was identified using comprehensive proteomic and metabolomic studies of otitis media using the chinchilla model.

11 Claims, 4 Drawing Sheets

(56) References Cited

OTHER PUBLICATIONS

Hetrick et al. "Small molecules CK-666 and CK-869 inhibit Arp2/3 complex by blocking an activating conformational change." Chem Biol, 2013, vol. 23(5), pp. 701-712.
Harmes et al. "Otits Media: Diagnosis and Treatment." Am Fam Physician, 2013, vol. 88(7), pp. 435-440.
Rodal et al. "Conformational changes in the Arp2/3 complex leading to actin nucleation,"Nat Struct Mol Biol, 2005, vol. 12(1), pp. 26-31.
Clementi et al. "Internalization and Trafficking of Nontypeable *Haemophilus influenzae*in Humann Respiratory Epithellal Cells and Roles of IgA1 Proteases for Optimal Invasion and Persistence" Infect Immun, 2014, vol. 82, No. 1, pp. 433-444.
Giganti et al. "Actin-filament cross-filament cross-linking protein T-plastin increases Arp2/3-mediated actin-based movement," J Cell Sci, 2004, vol. 118, pp. 1255-1265.
Hai et al. "Caldesmon phosphorylation in actin cytoskeletal remodeling." Eur J Cell Biol, 2006, vol. 85, pp. 305-309.
Edwards et al. "Capping Protein Regulators Fine-Tune Actin Assembly Dynamics." Nat Rev Mol Cell Biol, 2014, vol. 15(10), pp. 677-689.
Aerbajinal et al. "Glia maturation factory-γ negatively modulates TLR4 signaling by facilitating TLR4 endocytic trafficking in macrophages." J Immunol, 2013, vol. 190(12), pp. 6093-6103.
Fukuishi et al. "Does β-Hexosaminidase Function Only as a Degranulation Indicator in Mast Cells? The Primary Role of β-Hexosaminidase in Mast Cali Granules." J Immunol, 2014, vol. 193, pp. 1886-1894.
Bershadsky et al, "The state of actin assembly regulates actin and vinculin expression by a feedback loop." J Cell Science, 1995, vol. 108, pp. 1183-1193.
Szelestey, et al. "*Haemophilus*Responses to Nutritional Immunity: Epigenetic and Morphological Contribution to Biofilm Architecture, Invasion, Persistence and Disease Severity," PLoS Pathogens, 2013, vol. 9, issue 10, e1003709, pp. 1-17.

TREATMENT OF OTITIS MEDIA

GOVERNMENT FUNDING

This invention was made with Government support under Grant No. NIH NIDCD R01-DC013313 awarded by the National Institutes of Health. The Government has certain rights in the invention.

CROSS-REFERENCE TO RELATED APPLICATIONS

This application is the U.S. national phase entry of PCT/US2011/065752, with an international filing date of Sep. 11, 2015, which claims priority to U.S. Provisional Patent Application Ser. No. 62/048,953, filed Sep. 11, 2014, both of which are incorporated herein by reference.

BACKGROUND

Our current understanding of the global changes that occur during infection is primarily based upon transcriptional profiles of either the host or the bacteria. However, a significant component of disease progression is dependent upon posttranscriptional processes. Recent advances in the application of two-dimensional tandem mass spectrometry have dramatically increased sensitivity to allow simultaneous analyses of multiple molecules from very small biological samples. In this study, we report the comprehensive proteomic and metabolomic profiling of middle ear tissues using samples that are smaller than those typically obtained from a human biopsy. Proteomic and metabolomic analyses of samples as small as biopsies will revolutionize the elucidation of the mechanisms of pathogenesis in experimental models of disease as well as in human samples.

Otitis media (OM) is a significant disease of the pediatric population. The direct and indirect costs for the diagnosis and treatment of acute OM (AOM) in 2009 approached $3 billion and the number of all OM cases has estimated costs of treatment of up to $6 billion in the US annually. The scope of the problem is apparent with the observation that globally there are 709 million cases of AOM estimated per year of which 51% occur in children under the age of five. Monasta et al. (2012) PLoS One 7: e36226. Moreover, children attending daycare outside the home, approximated at 4 million children in the US in 2011, are 4-fold more likely to have an incidence of AOM. As a result, OM is the most common reason for a doctor's visit in school age children and is associated with significant morbidity. Long-term hearing loss is a direct consequence of untreated OM with effusion (OME). Clinical management of OM has relied heavily on antibiotic therapies (Auinger et al., (2003) Pediatrics 112: 514-520; Bauchner H, Philipp B (1998) Pediatrics 102: 142-145), which has contributed to the emergence of antibiotic resistant strains of bacteria. Novel solutions are needed for this highly prevalent disease and require extensive description of the molecular mechanisms of disease to define novel therapeutic targets.

Nontypeable *Haemophilus influenzae* (NTHI) predominates in approximately 50% of cases of AOM and has a significant role in OME. Holder et al. (2012) BMC Pediatr 12: 87. To better understand and ultimately prevent disease, it is imperative that we define the bacteria-host interaction during active disease. A chinchilla model of human OM has long been utilized to investigate the role of NTHI in OM. This animal model of disease has been successfully used to develop candidate vaccines aimed to prevent NTHI-mediated OM. Novotny et al., (2013) Vaccine 31: 3417-3426. In addition, mutational studies have identified NTHI gene products essential in bacterial pathogenesis. Harrison A, Santana E A, Szelestey B R, Newsom D E, White P, et al. (2013) Infect Immun 81: 1221-1233; Raffel et al., (2013) Infect Immun 81: 43-54. A limited number of transcriptional studies have assessed NTHI gene expression during OM. Whitby et al., (2013) BMC Genomics 14: 925; Mason et al., (2003) Infect Immun 71: 3454-3462. However, global analyses of the chinchilla model of OM have been limited, primarily due to the small amount of host material that can be retrieved from an animal and, until now, the absence of a chinchilla genome sequence. We have thus developed and successfully implemented analyses that assess global changes in proteins and metabolites in the chinchilla model of AOM. Using quantitative approaches, we identified a group of 105 proteins and 66 metabolites as potential targets in the development of rationally designed antimicrobial therapies. Moreover, these data represent the first global study of the host response during disease progression in vivo with techniques readily translatable to many diseases.

SUMMARY OF THE INVENTION

The inventors identified Actin-Related Protein 2/3 Complex (Arp2/3), a host protein strongly affected by nontypeable *Haemophilus influenza* (NTHI) infection. The inventors further demonstrated that loss of Arp2/3 function inhibited NTHI uptake by epithelial cells. On this basis, the present invention provides a method of treating otitis media in a subject by administering to the subject a therapeutically effective amount of an Arp2/3 inhibitor.

DETAILED DESCRIPTION OF THE INVENTION

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

Treat", "treating", and "treatment", etc., as used herein, refer to any action providing a benefit to a subject afflicted with a condition or disease such as otitis media, including improvement in the condition through lessening or suppression of at least one symptom, delay in progression of the disease, prevention or delay in the onset of the disease, etc.

Prevention, as used herein, refers to any action providing a benefit to a subject at risk of being afflicted with a condition or disease such as otitis media, including avoidance of infection or a decrease of one or more symptoms of the disease should infection occur.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

The term "antibody" as used herein refers to an immunoglobulin, whether natural or partly or wholly synthetically produced. The term also covers any polypeptide, protein or peptide having a binding domain that is, or is homologous to, an antibody binding domain. These can be isolated from natural sources, or may be partly or wholly synthetically produced. Examples of antibodies are intact immunoglobulin molecules, as well as to fragments thereof, such as Fab, F(ab')$_2$, Fc fragments, and single chain variable fragments (scFc), which are capable of binding an epitopic determinant. Antibody fragments refer to antigen-binding immunoglobulin peptides that are at least about 5 to about 15 amino acids or more in length, and that retain some biological activity or immunological activity of an immunoglobulin. Antibody as used herein includes polyclonal and monoclonal antibodies, hybrid, single chain, and humanized antibodies, as well as Fab fragments, including the products of an Fab or other immunoglobulin expression library, and suitable derivatives.

Treatment of Otitis Media Using Arp2/3 Inhibitors

In one aspect, the invention provides a method of treating otitis media in a subject. The method includes administering to the subject a therapeutically effective amount of an Actin-Related Protein 2/3 Complex (Arp2/3) inhibitor. In one embodiment, administration of the Arp2/3 inhibitor is effective to eliminate otitis media, while in another embodiment, administration of the Arp2/3 inhibitor is effective to decrease the severity of otitis media in the subject.

The subject to be treated by the methods of the invention suffers from or is at risk for otitis media. A subject has an increased risk for otitis media if the subject has an age of 4 or less, has been exposed to cigarette smoke, use of pacifiers, and is attending daycare. Otitis media is inflammation of the middle ear, or middle ear infection. Otitis media occurs in the area between the ear drum and the inner ear, including a duct known as the Eustachian tube. Methods of diagnosis of otitis media and clinical characteristics of the disease are known in the art. Thus, in some embodiments, the invention includes treatment methods whereby the individual to be treated is selected for treatment based on a diagnosis of otitis media (and in some embodiments, a diagnosis of a particular type of otitis media).

Otitis media typically involves dysfunction of the Eustachian tube. This is usually due to inflammation of the mucous membranes in the nasopharynx, which in turn can be caused by a viral upper respiratory tract infection (URI) or possibly by allergies. Because of the dysfunction of the Eustachian tube, the gas volume in the middle ear is trapped and parts of it are slowly absorbed by the surrounding tissues, leading to negative pressure in the middle ear. Eventually the negative middle-ear pressure can reach a point where fluid from the surrounding tissues is released in to the middle ear's cavity (also called tympanic cavity), causing a middle-ear effusion. Viral acute otitis media can occasionally lead to bacterial otitis media in a very short time, especially in children. *Streptococcus pneumoniae* and nontypeable *Haemophilus influenzae* are the most common bacterial causes of otitis media. Tubal dysfunction leads to the ineffective clearing of bacteria from the middle ear. Otitis media is usually diagnosed via visualization of the tympanic membrane in combination with the appropriate clinical history.

In one aspect, the invention encompasses methods to treat subjects suffering from a type of otitis media, selected from the group consisting of recurrent acute otitis media (RAOM), chronic otitis media with effusion (COME), acute post-tympanostomy otorrhea (APTO), chronic suppurative otitis media (CSOM), or choleastoma. The subject can have one or more of these types of otitis media. In some embodiments, the subject to be treated suffers from otitis media that is APTO. CSOM, or choleastoma. In other embodiments the subject to be treated suffers from APTO or CSOM. In one embodiment the individual suffers from CSOM.

"Acute otitis media" (AOM), as used herein, refers to a condition characterized by fluid in the middle ear accompanied by signs or symptoms of ear infection (bulging eardrum usually accompanied by pain; or perforated eardrum, often with drainage of purulent or infectious material). A subject with recurrent acute otitis media (RAOM) has had either more than three acute episodes in a period of six months or four or more acute episodes in a period of 12 months.

"Otitis media with effusion" (OME), as used herein, refers to a condition characterized by fluid in the middle ear without signs or symptoms of ear infection. Otitis media with effusion is defined as chronic (COME) when middle ear effusion has been present for at least 3 months.

"Chronic suppurative otitis media" (CSOM), as used herein, differs from "chronic otitis media with effusion" (COME) with respect to the state of the tympanic membrane. Chronic otitis media with effusion (COME) may be defined as a middle ear effusion, without perforation of the tympanic membrane, which is reported to persist for 3 months. Chronic suppurative otitis media is a perforated tympanic membrane with persistent drainage from the middle ear.

"Acute post-tympanostomy otorrhea" (APTO), as used herein, refers to a condition characterized by the presence of purulent fluid or inflamed middle ear mucosa occurs following tympanostomy tubes placement. Drainage following tube placement that persists for less than 8 weeks, is classified as acute.

Arp2/3 Inhibitors

The invention provides a method of treating otitis media by administering a therapeutically effective amount of an Actin-Related Protein 2/3 Complex (Arp2/3) inhibitor to a subject. The Arp2/3 complex is a seven-subunit assembly that nucleates branched actin filaments. Rotty et al., Nature Reviews Molecular Cell Biology 14, 7-12 (2013).

A variety of different types of Arp2/3 inhibitors are suitable for use in the method of treating otitis media. Suitable Arp2/3 inhibitors include small molecule organic compounds that bind to Arp2/3, antibodies specific for Arp2/3, proteins that interact with Arp2/3 such as Arpin (Gorelik et al., Med Sci (Paris), 30(3):248-50 (2014)) and nucleotides such as siRNA, antisense RNA, RNA aptamers, or ribozymes that interfere with the expression of Arp2/3. In some embodiments, the Arp2/3 inhibitor is a small molecule organic compound. Examples of small molecule Arp2/3 inhibitors include the compounds CK-636, CK-666, CK-548, and CK-869. See Nolen et al., Nature, 460, 1031-1035 (2009); and Hetrick et al., Chem Biol. 20, 701-712 (2013), the disclosures of which are incorporated herein by reference. The structures of the compounds are shown below:

CK-636

CK-666

CK-548

CK-869

The subject is preferably a mammal, such as a domesticated farm animal (e.g., cow, horse, pig) or pet (e.g., dog, cat). More preferably, the subject is a human. Alternately or in addition, Arp2/3 inhibitors can be administered prophylactically to a subject prior to the development of otitis media. For example, Arp2/3 inhibitors can be administered to a subject who has an increased risk of developing otitis media, such as a subject having an upper respiratory infection. Prophylactic administration, also referred to as prevention, is effective to decrease the likelihood of the subsequent disease in the subject, or decrease the severity of otitis media that subsequently occurs.

Candidate Arp2/3 inhibitors may be tested in animal models. For example, Arp2/3 inhibitors can be tested using the bronchial epithelial cell infection model, or the chinchilla model of human otitis media, as described herein. Candidate compounds can also be tested for their ability to inhibit actin polymerization. Nolen et al., Nature, 460, 1031-1035 (2009). Results are typically compared between control animals treated with candidate agents and the control littermates that did not receive treatment. Candidate agents can be used in these animal models to determine if a candidate agent decreases one or more of the symptoms associated with otitis media.

In other embodiments of the invention, antibodies specific for a portion of the Arp2/3 complex can be prepared for use as Arp2/3 inhibitors. Polyclonal antibodies are heterogeneous populations of antibody molecules that can be obtained from the sera of animals immunized with an antigen. The antigen can be Arp2/3, or an effective fragment thereof. In order to be useful, a peptide fragment of Arp2/3 must contain sufficient amino acid residues to define the epitope of Arp2/3. To facilitate generation of the antibodies, the substrate peptides can be coupled to a carrier protein such as KLH as described in Ausubel et al. (1989) Current Protocols in Molecular Biology, John Wiley & Sons, New York. Using this method, the KLH-peptide is mixed with Freund's adjuvant and injected into guinea pigs, rats, donkeys and the like or preferably into rabbits, thereby stimulating formation of antibodies to the peptide (e.g., the Arp2/3 complex).

Monoclonal antibodies can be prepared using the Arp2/3 complex or an antigenic fragment thereof using standard hybridoma technology (see e.g. Kohler el al., (1975) Nature 256:495; Hammerling et al., (1981) In Monoclonal Antibodies and T Cell Hybridomas, Elsevier, New York). For example, monoclonal antibodies to Arp2/3 can be raised in Balb/C or other similar strains of mice by immunization with purified or partially purified preparations of the Arp2/3 complex. The spleens of the mice can be removed, and their lymphocytes fused to a mouse myelonia cell line. After screening of hybrids by known techniques, a stable hybrid will be isolated that produces antibodies against a portion of the Arp2/3 complex. The activity of the antibodies can be demonstrated by their ability to prevent the binding of radiolabelled Arp2/3 (or vice versa), or their ability to inhibit the biological activity of Arp2/3. Once produced, monoclonal antibodies can be tested for recognition of a specific antigen of Arp2/3 by Western blot or immunoprecipitation analysis.

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. Coding, Monoclonal Antibodies: Principles and Practice, 2d ed., pp. 104-126, Orlando, Fla. Academic Press.

Antibodies and antibody fragments specific for Arp2/3 can be used as Arp2/3 inhibitors. Antibodies are designed for specific binding, as a result of the affinity of complementary determining region of the antibody for the epitope of the target molecule (e.g., Arp2/3). An antibody "specifically binds" when the antibody preferentially binds a target structure, or subunit thereof, but binds to a substantially lesser degree or does not bind to a biological molecule that is not a target structure. For example, an antibody specific for Arp2/3 can be an antibody or antibody fragment capable of binding to an Arp2/3 complex with a specific affinity of between 10"M and 10-" M. In some embodiments, an antibody or antibody fragment binds to Arp2/3 with a specific affinity of greater than $10^{-7}$M, $10^{-8}$M, $10^{-9}$M, $10^{-10}$M, or $10^{-11}$M, between $10^{-8}$M-$10^{-11}$M, $10^{-9}$M-$10^{-10}$, and $10^{-10}$M-$10^{-11}$M. In a preferred aspect, specific activity is measured using a competitive binding assay as set forth in Ausubel F M, (1994). Current Protocols in Molecular Biology. Chichester: John Wiley and Sons ("Ausubel"), which is incorporated herein by reference.

Otitis media is typically caused by an upper respiratory tract infection, which can involve bacterial or viral infection. In addition, viral infection can sometimes lead to bacterial infection. Accordingly, in some embodiments, the subject has a bacterial infection in addition to having otitis media, or being at risk of developing otitis media. Most cases of otitis media are caused by one of three major pathogens. These are *Streptococcus pneumoniae, Haemophilus influenzae*, and *Moraxella catarrhalis*. Accordingly, in some embodiments, the bacterial infection represents infection primarily by one of these pathogens. In some embodiments, the invention is useful for treating otitis media caused by nontypeable *Haemophilus influenzae*.

Because otitis media often includes bacterial infection, it may be advantageous to administer an antibiotic to a subject in addition to an Arp2/3 inhibitor. Antibiotics include macrolide antibiotics, penicillins, tetracyclines, cephalosporins, quinolones, fluoroquinolones, neomycin, gentamycin, and vancomycin. See Harmes et al., Am Fam Physician. 2013 Oct. 1; 88(7):435-40, the disclosure of which is incorporated herein by reference. In some embodiments, the antibiotic is selected from the list consisting of amoxicillin, rifampicin, ciprofloxacin, azithromycin, clarithromycin, ceftriaxone, cefuroxime, and cefotaxime.

In some embodiments, the antibiotic and the Arp2/3 inhibitor are administered concomitantly. Concomitant, as used herein, means that the two drugs are administered either in combination or that the antibiotic is administered separately while the Arp2/3 inhibitor is present in a therapeutically effective amount.

Administration, Dosage, and Formulation

The present invention also provides pharmaceutical compositions that include an Arp2/3 inhibitor, and in some cases an antibacterial agent, as active ingredient(s), and a pharmaceutically acceptable liquid or solid carrier or carriers, in combination with the active ingredient. The pharmaceutical compositions include one or more active agents together with one or more of a variety of pharmaceutically acceptable carriers for delivery to a subject, including a variety of diluents or excipients known to those of ordinary skill in the art.

It is envisioned that the pharmaceutical composition can be administered to any type of infection, by injection, topically, or even orally. For the treatment of otitis media, the pharmaceutical composition may be administered to the ear or the sinuses. The administration may be from the outer ear to the middle ear, e.g. to a patient whose ear drum is pierced and a grommet inserted. Alternatively, if the infection is otitis externa, the administration may be via ear drops. If the infection is of the middle ear, the ear drops may contain a substance which allows permeabilization of the active ingredient(s) across the ear drum. In a further embodiment, the drug may be administered orally, intransally, intravenously, intramuscularly, in the tear ducts, or by inhalation.

Substances which may be used to permeabilize the ear drum and allow entry of the active ingredients may be any substance which increases the permeability of membranes, such as those which are used to permeabilize skin in dermatology. Examples of such substances include, but are not limited to dimethylsulfoxide (DMSO), dimethylacetamide, methyldecyl sulfoxide, cotton seed oil, caster oil derivatives, fatty acid esters, glycerol, vesicles, liposomes, silicone vesicles (see U.S. Pat. No. 5,364,633 herein incorporated by reference), anionic surfactants, preparations such as those in U.S. Pat. No. 5,500,416, herein incorporated by reference.

The dosage of the active ingredient(s) may vary with the method of administration and the severity of the condition to be treated. In general, however, a dosage of from about 0.1 to 100 mg/kg/dose, and more preferably 0.5 to 50 mg/kg/dose of the drug administered 1 to 8 times a day by the intranasal route, or from 1 to 10 drops of a solution or suspension administered from 1 to 10 and preferably 1 to 6 times a day, to each ear. In a further embodiment, from about 0.01 mg/ml to about 100 mg/hl, including, but not limited to 0.1 mg/ml, 1 mg/ml, 2, mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 30 mg/ml, 40 mg/ml, 50 mg/ml, 60 mg/ml, 70 mg/ml, 80 mg/ml, and 90 mg/ml is administered to the ear, sinuses, or upper respiratory tract at least one time per day. Local administration is preferable because it reduces the chances of unwanted side-effects. However, for systemic administration, a dose of from about 0.01 mg/ml to about 1 g/ml may be administered at least one time per day for at least and including one day. Useful dosages of the active agents can be determined by comparing their in vitro activity and the in vive activity in animal models. Methods for extrapolation of effective dosages in mice, and other animals, to humans are known in the art; for example, see U.S. Pat. No. 4,938,949.

The composition for administration may additionally include additives, excipients, thickeners, and other substances which allow for more effective administration. Examples include oils, emollients, or other substances which increase the effectiveness and comfort of ear drops, nasal sprays, and inhalable compositions. This may also include substances which enhance the smell or taste.

Additional pharmaceutical methods may be employed to control the duration. Controlled release preparations may be achieved through the use of polymers to complex or adsorb the composition. Alternatively, it is possible to entrap the composition into microcapsules, vesicles, or comparable molecules.

The present invention is illustrated by the following examples. It is to be understood that the particular examples, materials, amounts, and procedures are to be interpreted broadly in accordance with the scope and spirit of the invention as set forth herein.

EXAMPLES

Example 1: Comprehensive Proteomic and Metabolomic Signatures of Nontypeable Haemophilus influenzae-Induced Acute Otitis Media Reveal Bacterial Aerobic Respiration in an Immunosuppressed Environment A thorough understanding of the molecular details of the interactions between bacteria and host are critical to ultimately prevent disease. Recent technological advances allow simultaneous analysis of host and bacterial protein and metabolic profiles from a single small tissue sample to provide insight into pathogenesis. We used the chinchilla model of human otitis media (OM) to determine, for the first time, the most expansive delineation of global changes in protein and metabolite profiles during an experimentally induced disease. After 48 hours of infection with nontypeable Haemophilus influenzae (NTHI), middle ear tissue lysates were analyzed by high-resolution quantitative two-dimensional liquid chromatography-tandem mass spectrometry. Dynamic changes in 105 chinchilla proteins and 66 metabolites define the early proteomic and metabolomic signature of OM. Our studies indicate that establishment of disease coincides with actin morphogenesis, suppression of inflammatory mediators and bacterial aerobic respiration. We validated the observed increase in the actin-remodeling complex, Arp2/3 and experimentally demonstrated a role for Arp2/3 in NTHI invasion. Direct inhibition of actin branch morphology altered bacterial invasion into host epithelial cells, and is supportive of our efforts to utilize the information gathered to modify outcomes of disease. The twenty-eight NTHI proteins identified participate in carbohydrate and amino acid metabolism, redox homeostasis and include cell wall-associated metabolic proteins. Quantitative characterization of the molecular signatures of infection will redefine our understanding of host response driven developmental changes during pathogenesis. These data represent the first comprehensive study of host protein and metabolite profiles in vive in response to infection and show the feasibility of extensive characterization of host protein profiles during disease. Identification of novel protein targets and metabolic biomarkers will advance development of therapeutic options for treatment of disease.

Methods

Arp2/3 expression in NTHI infected mucosae—Western blot analysis: Protein concentrations of middle ear mucosal lysates from NTHI infected and sham-treated animals were quantified using Bradford's reagent. Mucosal lysates were mixed with Laemmli sample buffer, boiled for 10 minutes, and ~100 ng of each sample resolved on a 12% SDS-polyacrylamide gel. Proteins were then transferred to a nitrocellulose membrane by electrophoresis and the membrane probed with an anti-human Arp2/3 complex antibody (EMD Millipore, Billerica, Mass.) and horse radish peroxidase (HRP) conjugated to goat anti-mouse IgG (Life Technologies) and detected using a chemiluminescent substrate ECL (GE Healthcare, Pittsburgh, Pa.).

Arp2/3 expression in NTHI infected mucosae-immunohistochemistry: Arp23 was visualized in situ as follows. Paraffin embedded sections of middle cars from sham-treated and NTHI-infected chinchillas were deparaffinized in xylene then rehydrated step wise in graded alcohols (three times in 100% ethanol, once in 95% ethanol), then placed in water. Slides were then placed in Antigen Retrieval AR-10 Solution (Biogenex, Premont, Calif.) and rapidly boiled for 15 minutes by microwaving. After cooling, slides were washed twice with water, then twice with DPBS. Unless noted otherwise, slides were washed twice with DPBS between all steps. Slides were blocked for 10 minutes with 0.01% sodium borohydride blocked for a further 10 minutes with CAS-Block Histochemical Reagent (Life Technologies), then directly incubated for 30 minutes in Image-iT FX Signal Enhancer (Life Technologies). Slides were then incubated overnight with anti-human Arp2/3 complex antibody diluted 1:5000 in CAS-Block Histochemical Reagent followed by a 1 hour incubation with Protein A conjugated with Alexa Fluor 488 (Life Technologies) diluted 1:100 in CAS-Block Histochemical Reagent. Slides were stained with wheat germ agglutinin (WGA)-Alexa Fluor 594 (LifeTechnologies), followed by Hoescht 33342 (Life Technologies) and examined by fluorescent microscopy using an Axiovert 200M inverted epifluorescence microscope equipped with an Axiocam MRM CCD camera (Carl Zeiss Inc., Thornwood, N.Y.).

Inhibition of Arp2/3—Normal human bronchial epithelial cell (NHBE) infection model: NHBE cells (Lonza, Walkersville, Md.) were seeded into 24-well plates containing sterile coverslips and grown in Bronchial Epithelial Cell Growth Medium (BEGM; Lonza, Walkersville, Md.) at 37° C. in a 5% $CO_2$ atmosphere to near confluency. The OFP-expressing strain of NTHI strain 86-028NP(pGM1.1) (Vogel et al. (2012) Frontiers in Cellular and Infection Microbiology 2) was grown overnight at 37° C., in a 5% $CO_2$ atmosphere on chocolate II agar plates. The next morning the colonies were re-suspended in brain heart infusion broth supplemented with 2 μg/ml heme and 2 μg/ml β-NAD (sBHI) and grown at 37° C. with shaking at 180 rpm until the cells were in mid-log phase (~5 generations). Prior to infection, the BEGM was removed from the NHBE cells and replaced with BEGM that contained either 200 μM CK-636 (Sigma-Aldrich, St. Louis, Mo.), an inhibitor of Arp2/3 function, or 0.2% DMSO, the vehicle for CK-636. Strain 86-028NP(pGM1.1) was then added to the NHBE cells at a multiplicity of infection of 50 bacteria to one NHBE cell and incubated at 37° C. in a 5% $CO_2$ atmosphere for one hour. The NHBE cells were then washed twice with DPBS before being placed back in BEGM that contained either 200 μM CK-636 or 0.2% DMSO. Cells were incubated at 37° C. in a 5% $CO_2$ atmosphere for 24 or 48 hours. At each time point, cells were stained with WGA-Alexa Fluor 594, fixed in 4% paraformaldehyde (Electron Microscopy Sciences, Hatfield, Pa.) in DPBS, permeabilized with 0.1% Triton X-100 then stained with phalloidin-Alexa Fluor 350. The NHBE cells were examined by fluorescent microscopy using an Axiovert 200M inverted epifluorescence microscope equipped with an Axiocam MRM CCD camera. Experiments were repeated in triplicate and representative examples are shown.

Results

Figure 1:
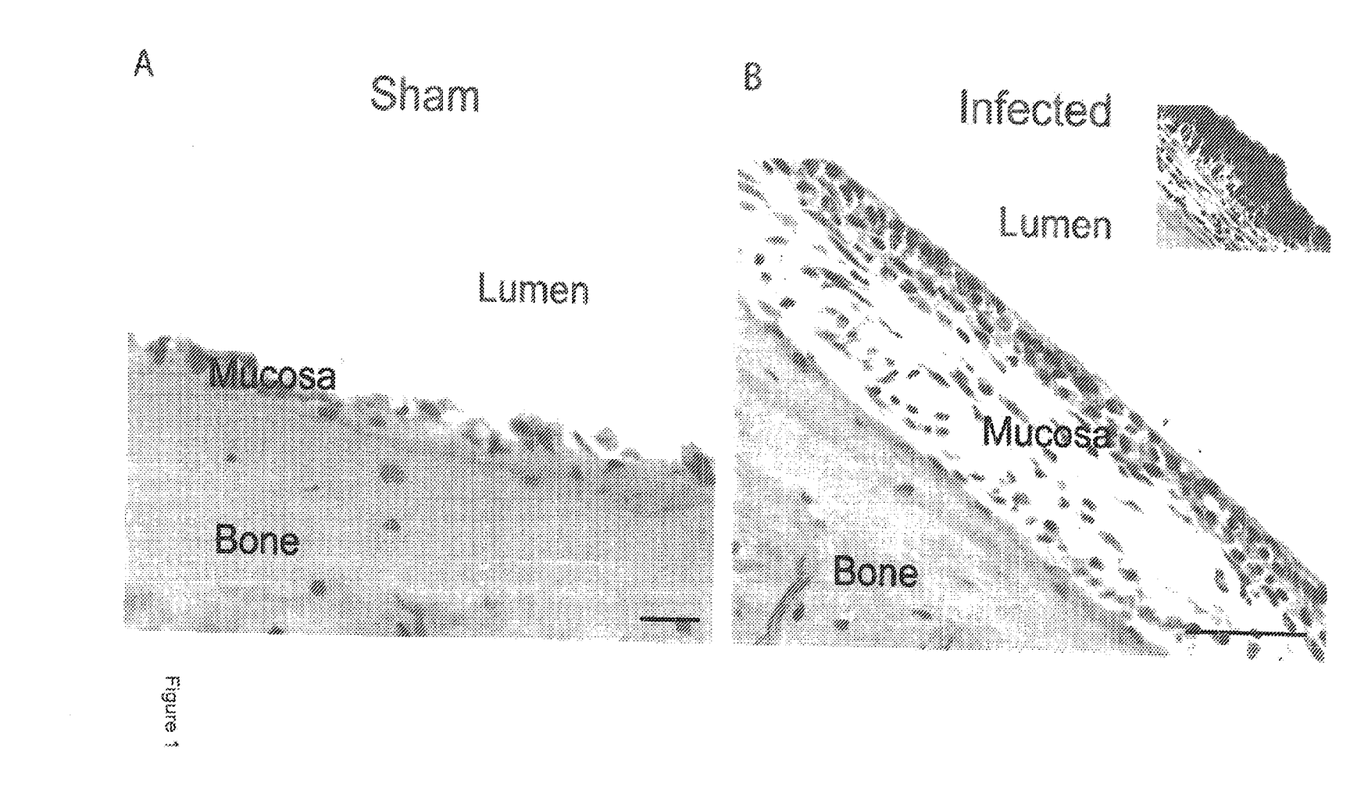
FIG. 1 provides images showing the infection of chinchilla middle ears demonstrating that NTHI influences host-bacterial responses. Images are representative of chinchilla middle ears inoculated with NTHI (Infected) or sterile saline (Sham). Histopathology was assessed two days after inoculation by examination of hematoxylin stained thin sections while glycan and mucin production was assessed by examination of Periodic acid-Schiff (PAS) stain. Inset depicts positive PAS labeling of chinchilla middle ear epithelium from a time point later in infection. Mucin is readily identified at the interface of the mucosae and the lumen. Scale bar=50 μm.

Descriptive analysis of the experimental AOM proteome: We determined the proteomic profiles by LC/LC-MS/MS of 3 µg middle ear tissue infected for 2 days with NTHI for comparison with sham treated middle ear tissues (FIG. 1). The release of the chinchilla genome sequence provided the platform for improved accuracy in identification of the proteomic profiles in this model system. Approximately 60% of the total protein mass consists of 25 proteins. Similar to other studies of serum/plasma, cerebrospinal fluid or bronchoalveolar lavage fluid (Foster et al. (2013) J Proteome Res 12: 2194-2205), the middle ear exhibits a large dynamic range of protein abundance (e.g. albumin, hemoglobin, serotransferrin, other serum proteins). Despite this complexity of the in vivo model system, we identified and obtained differential quantitative information for peptides derived from 377 proteins involved in such processes as: actin filament morphogenesis, inflammation, substrate binding, oxidative stress, vesicular transport as well as neutrophil associated proteins, indicating early neutrophil infiltration.

NTHI infection of chinchilla middle ears induces transcriptional changes that mirror changes in protein amount: qRT-PCR was used to confirm that the changes in the amount of select proteins due to AOM caused by NTHI were due to changes in transcription. RNA was purified from middle ear tissue of both sham-treated and NTHI infected chinchillas collected concurrently with the tissues used in the proteomic and metabolomic studies. Although these tissues were limited in number, sufficient RNA was isolated to test expression of seven genes. In all cases, changes in gene expression due to NTHI infection showed a similar trend to changes in the amount of protein detected.

Figure 2:
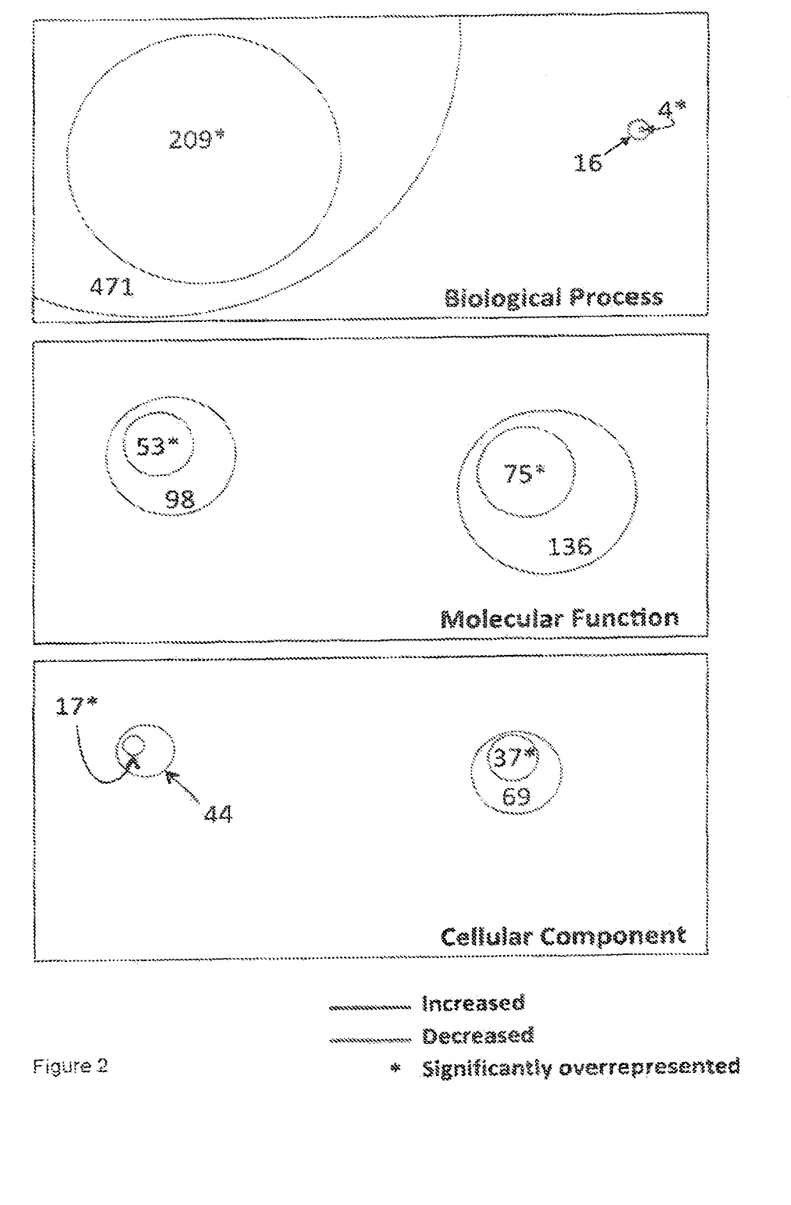
FIG. 2 provides a graphical summary of overrepresented proteins categorized by gene ontology (GO) function. Genes that encoded proteins that were increased or decreased in amount due to NTHI-induced AOM were categorized by GO. For each ontological group; the number of nodes generated are represented by the larger circles while the number of nodes that are the overrepresented subset are shown as the smaller circles. The size of each circle is scaled to the number of nodes contained within.

Gene Ontology Analyses: The levels of 105 proteins changed significantly (44 proteins increased, 61 proteins decreased) due to infection with NTHI. BLAST analysis showed strong identity between the chinchilla proteins and their human orthologs. Chinchilla proteins that exhibited changes in production after NTHI infection could thus be categorized with Gene Ontology (GO) tools designed for the analyses of human data. The Biological Networks Gene Ontology tool [BiNGO; Maere et al., (2005) Bioinformatics 21: 3448-3449] identified proteins overrepresented within three ontologies: biological process, molecular function or cellular component and visualized with Cytoscape. These analyses identified nodes significantly overrepresented within each data set (FIG. 2). Within biological processes, overrepresented nodes that contain upregulated proteins are primarily related to host immune functions while nodes that represent downregulated proteins encompass small molecule metabolic and catabolic processes, response to chemical stimuli and the cellular response to calcium. Fox molecular functions, upregulated proteins are in nodes that represent carbohydrate, polysaccharide, bacterial cell surface, calcium, actin and actin-filament binding. Conversely, proteins downregulated are in nodes of which 40% are related to aspects of oxidoreductase activity and 29% are involved in molecular binding. For cellular components, seven nodes for upregulated proteins contained proteins with roles in actin filament morphogenesis and actin-related functions. Finally, for the cellular component proteins whose levels decreased due to NTHI infection, approximately one-third of the associated nodes have roles in actin-myosin based functions.

Actin filament regulation in AOM: Actin cytoskeleton plasticity is critical for many cellular functions. Song et al. (2013) Immunol Rev 256: 177-189. During NTHI-induced AOM in the chinchilla, 14 of the 105 proteins identified participate in actin morphogenesis. Within this subset of proteins, seven exhibited increased levels, while seven exhibited decreased levels (Table 1). At this stage of the infection, actin rearrangements could be involved in epithelial cell proliferation, immune cell migration or phagocytosis of NTHI.

TABLE 1

Actin-related proteins whose amounts changed due to NTHI infection

| Protein accession no. | Function | Peptide match | Fold change of Infected/sham | p-value |
| --- | --- | --- | --- | --- |
| XP_005399838.1 | Gila maturation factor gamma isoform X1 | 2 | 2.9 | 2.5132E−05 |
| XP_005413091.1 | actin-related protein 2/3 complex subunit 4 | 7 | 2.8 | 7.17E−07 |
| XP_005380964.1 | destrin | 2 | 2.6 | 2.41E−05 |
| XP_005409156.1 | plastin-2 | 18 | 2.6 | 3.81E−06 |
| XP_005397993.1 | actin-related protein 2/3 complex subunit 1B isoform X3 | 5 | 2.5 | 3.51E−05 |
| XP-00540524.1 | coronin-1A | 10 | 2.3 | 7.17E−05 |
| XP-005388181.1 | F-actin-capping protein subunit alpha-2 | 3 | 2.1 | 1.88E−03 |
| XP_005393859.1 | tropomyosin alpha-4 chain isoform X8 | 5 | −2.1 | 1.46E−04 |
| XP-005415261.1 | neuroblast differentiation-associated protein | 4 | −2.4 | 7.89E−07 |
| XP_005409541.1 | tropomyosin alpha-4 chain | 2 | −2.5 | 4.25E−04 |
| XP_005405560.1 | non-muscle caldesmon isoform X7 | 4 | −2.5 | 2.75E−06 |
| XP-005414854.1 | neuroblast differentitation-associated protein | 10 | −2.6 | 7.89E−07 |
| XP_005380714.1 | dihydropyrimidinase-related protein 3 isoform X2 | 4 | −4.6 | 4.00E−05 |
| XP_005392735.1 | beta-actin-like protein 2 isoform X2 | 2 | −4.7 | 2.03E−04 |

Figure 3:
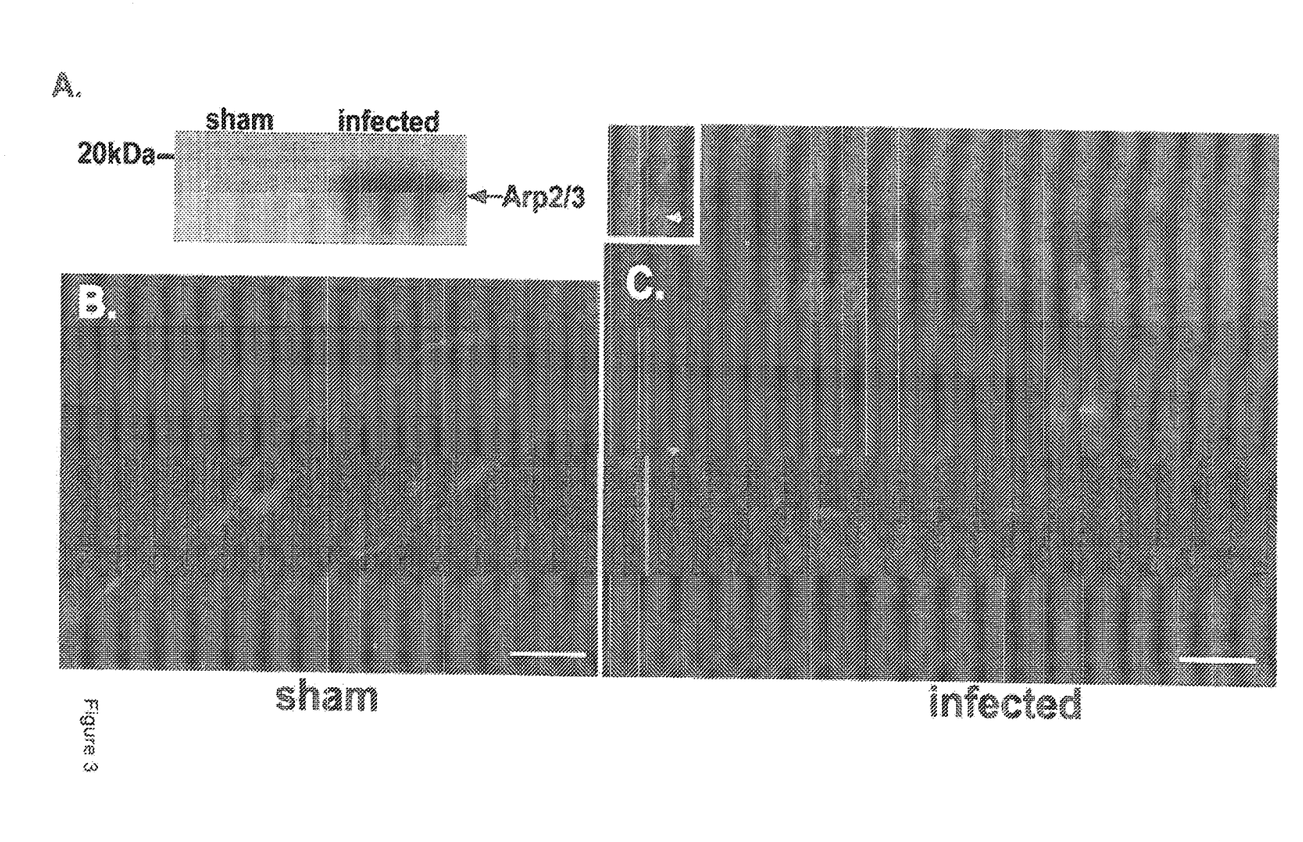
FIG. 3 (A. B) provides images showing Arp2/3 production increased in middle ear mucosae of chinchillas with AOM. (A) Immunoblot analysis of chinchilla middle ear mucosae lysates resolved by SDS-polyacrylamide gel electrophoresis. A representative image shows detection of Arp2/3 in tissue from an infected but not in a sham-treated animal. Arp2/3 was also visualized in middle ear sections isolated from sham treated (B) or NTHI infected (C) chinchillas. The Arp2/3 complex was labeled with an anti-human Arp2/3 monoclonal antibody and detected with Alexa Fluor 488-conjugated Protein A. Host cell membranes were stained with wheat germ agglutinin conjugated to Alexa Fluor 594. DNA was counterstained with Hoechst 334580 (white). Arrows indicate Arp2/3 on the leading edge of immune cells.
Figure 4:
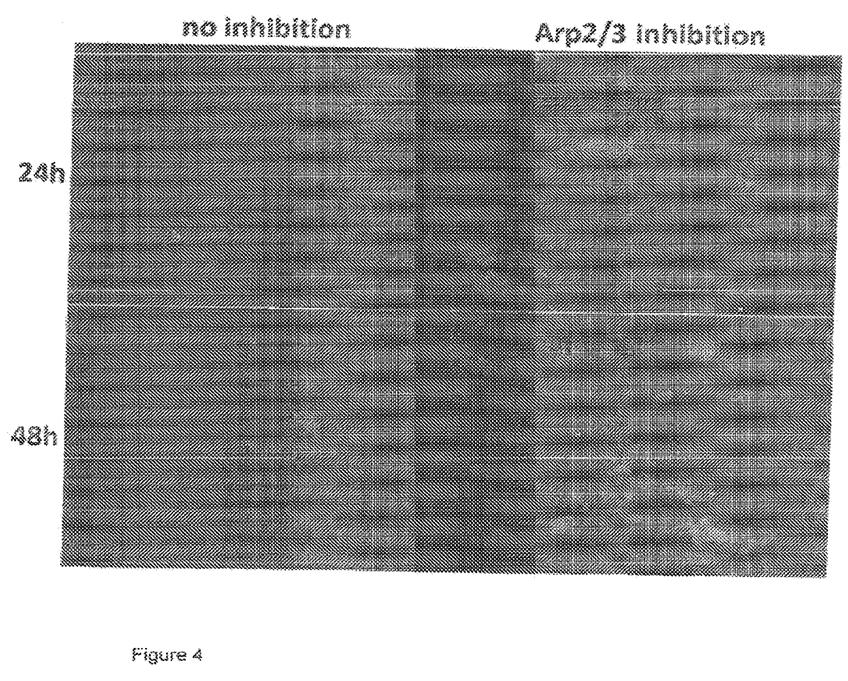
FIG. 4 provides an image showing inhibition of Arp2/3 reduced NTHI invasion into epithelial cells. Normal human bronchial epithelial cells were treated with the Arp2/3 inhibitor CK-636 then inoculated with NTHI expressing GFP. After 24 or 48 hours, actin was visualized using fluorescently labeled phalloidin-Alexa Fluor 350 and cell membranes were visualized using wheat germ agglutinin-Alexa Fluor 594.

Role of actin morphogenesis in NTHI invasion into epithelial cells: To investigate the biological consequences of actin morphogenesis in epithelial cells, we evaluated the contribution of the actin-related protein complex, Arp2/3, in NTHI invasion. Arp2/3 is comprised of two actin-like proteins (Arp2, Arp3) and five accessory proteins (ArpC1-5). This complex has a critical role in the nucleation of branched actin structures to generate force at the lamellipodia, within phagocytic cups, for endocytic vesicle morphogenesis and autophagy, amongst others. Rodal et al. (2005) Nat Struct Mol Biol 12: 26-31. Two of the subunits of the Arp2/3 complex (ArpC1, ArpC4) demonstrated increased levels in middle ears infected with NTHI, as compared to sham-infected middle ears. The increase in Arp2/3 levels observed in infected tissues was validated by immunoblot analysis of mucosal lysates (FIG. 3). Moreover, immunohistochemistry of middle ear inferior bullae demonstrated bright punctate staining of Arp2/3 that was readily apparent at the leading edges of neutrophils within the NTHI biofilm. In addition, Arp2/3 was occasionally observed at the periphery of cells within the middle ear mucosae and in the few neutrophils that could be detected within tissue isolated from a sham treated animal (FIG. 3). A role for Arp2/3 in epithelial cell actin remodeling in response to NTHI infection was evaluated through the inhibition of Arp2/3 function with the small molecule CK-636. Nolen et al. (2009) Nature 460: 1031-1034. Consistent with previous reports (Raffel et al., (2013) Infect Immun 81: 43-54), viable internalized NTHI were not observed in NHBE cells following 24 and 48 hours of infection. When Arp2/3 function was inhibited, we observed gross morphological changes in actin structure and an increase in the number of extracellular bacteria indicating that bacterial uptake was reduced (FIG. 4). These data suggest that Arp2/3 participates in NTHI internalization with subsequent intracellular trafficking to the endolysosomal pathway. Clementi et al., (2014) Infect Immun 82: 433-444.

Action of Actin-Associated Proteins Identified During AOM

Regulation of actin ultrastructure: We observed increased levels of proteins [e.g. glia maturation factor G (GMFG), coronin-1A, cofilin, L-plastin] (Table 1) that have predicted roles in the production of new actin filaments, in concert with the destabilization of existing actin filaments, primarily through interactions with Arp2/3. Giganti el al. (2005) J Cell Sci 118: 1255-1265. Consistent with the plasticity of actin polymerization at this time point, we also observed decreases in levels of proteins (e.g. caldesmon, CapZA) that have predicted roles in the stabilization of actin filaments. Hai C M, Gu Z (2006) Eur J Cell Biol 85: 305-309. Actin capping proteins are thus critical to direct local polymerization to facilitate lamellipodia formation and motility and cell velocity. Edwards et al. (2014) Nat Rev Mol Cell Biol 15: 677-689. Taken together, we suggest that the changes in these protein profiles observed during AOM will result in the net destabilization of actin polymers to facilitate actin filament remodeling and branch formation.

Discussion

Rationale for a multi-omics approach to the study of disease: The drive to understand disease has become increasingly dependent on multi-faceted approaches. Identification of proteins and metabolites from the same sample provides a cross platform validation of the analysis of the host-pathogen interactions that influence disease progression. We used the chinchilla model to compare the protein and metabolite signatures in chinchillas with NTHI-induced AOM compared with sham treated chinchillas. We observed striking differences in the architecture of the middle ear mucosal tissue as well as early infiltration of immune cells in the chinchillas that developed experimental OM as compared to sham treatment (FIG. 1). Using a small tissue sample, we showed that this multifaceted approach is possible for the identification of both therapeutic targets and biomarker of a human disease. In addition to the small sample size, our approach demonstrates the feasibility of using outbred animals in the identification of significantly changed molecules. Therefore, this approach is amenable to other experimental models of disease as well as with human samples.

Actin morphogenesis in pathogenesis and immune signaling: Approximately 13% of chinchilla proteins that exhibited significant changes in amount due to AOM were involved in actin morphogenesis. The changes observed will likely lead to depolymerization, debranching and a reduction in bundling of actin filaments, mechanisms that increase the pool of monomeric actin for subsequent actin cytoskeleton morphogenesis. As well as contributing to these structural functions, actin related proteins also participate in regulation of host cell signaling in response to bacteria. GMPG negatively regulates lipopolysaccharide (LPS) induced activation of the NF-κB, MAPK and IRF3 signaling pathways in macrophages through the control of endosomal sorting of TLR4 Aerbajinai et al., (2013) J Immunol 190: 6093-6103. GMFG can also stimulate neutrophil migration and polarity, while coronin-1A and L-plastin control neutrophil phagocytosis and CD18 activation, respectively. Coronin-1A is localized to phagocytic vacuoles of neutrophils where the actin cytoskeleton mediates both phagocytic killing and binds p40$^{phox}$ to activate NADPH oxidase driven production of superoxide. This latter process is also plastin mediated. Plastins further participate in cell invasion by the intracellular pathogens *Salmonella typhimurium* and *Shigella flexneri*. Delanote el al., (2005) Acts Pharmacol Sin 26: 769-779. Similarly. AHNAK complexes with actin, S100A10 and annexin A2 to mediate architectural remodeling of the cell membrane and cortical cytoskeleton to promote invasion of *Salmonella Typhimurium* into epithelial cells. Our observation of increased levels of these actin-associated proteins implicates actin remodeling in the enhanced recruitment of immune cells and invasion of epithelial cells. Concurrent with this hypothesis, we observed a significant decrease in the lysosomal enzyme hexosaminidase B that plays a role in degradation of internalized bacteria. Fukuishi el al. (2014) J Immunol 193: 1886-1894.

Actin morphogenesis and T and B cell function: Actin related proteins help regulate T and B cells, although the biological role of T cells in early AOM are unknown. Both AHNAK and coronin-1A control T cell differentiation and activation through regulation of the actin cytoskeleton. Interestingly, coronin-1A blocks Arp2/3 and Wiskott-Aldrich syndrome family protein binding of actin at the immune synapse. This blockade impairs T cell migration and alters T cell modulation of the NF-κB pathway. Moreover, L-plastin directs the polarization of T cells towards antigen presenting cells to generate an immune synapse at the point of cell contact. L-plastin dependent localization of CCR7 at the leading edge during T cell polarization is critical for chemotaxis and cytokine production. Finally, L-plastin is required for chemokine-mediated B cell maturation and migration and the production of follicular and marginal zone B cells. Taken together, these data suggest that T cell activation and migration signaling events occur early during infection of the middle ear.

Biological consequences of actin-associated proteins during pathogenesis: The regulatory systems described generate precise control of actin filament and network formation.

Moreover, the cell must be able to sense and respond to both external and internal signals and modulate actin remodeling accordingly, as a critical part of the host response to infection. During AOM, the host initiates both innate and adaptive responses to NTHI infection and changes in the actin cytoskeleton will be critical to these processes. Host defense cells migrate to the site of infection and prepare to neutralize bacteria through phagocytosis and induction of adaptive immunity. Preparatory to these actions, host cells will disassemble existing filamentous actin structures to increase the pool of monomeric actin, which is used in the polymerization of new actin filaments critical to many immune processes. In concert, the increase in monomeric actin will repress actin expression via an autoregulatory pathway. Bershadsky el al. (1995) J Cell Sci 108 (Pt 3): 1183-1193.

The importance of actin morphogenesis during NTHI infection of the middle ear was demonstrated by our proof-of-concept study in which the function of Arp2/3 was inhibited. In addition to potential roles in immune cell function, we demonstrated that Arp/2/3 plays important roles in NTHI invasion into NHBE cells. We have previously shown that the NTHI responses to nutritional immunity promote intracellular invasion and survival within host cells. Szelestey et al., (2013) PLoS Pathog 9: e1003709. We therefore suggest that therapeutic modulation of actin remodeling would prevent invasion and increase the vulnerability of NTHI to the host immune responses and antibiotic therapies.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through which the compounds are effective, the inventors are not bound by theories described herein. The invention is not limited to the exact details shown and described, for variations obvious to one skilled in the art will be included within the invention defined by the claims.

What is claimed is:

1. A method of treating otitis media in a subject, comprising administering to the subject a therapeutically effective amount of an Actin-Related Protein 2/3 Complex (Arp2/3) inhibitor.

2. The method of claim 1, wherein the Arp2/3 inhibitor is small molecule organic compound.

3. The method of claim 2, wherein the Arp2/3 inhibitor is selected from the group consisting of CK-636, CK-666, CK-548, and CK-869.

4. The method of claim 1, wherein the subject has a bacterial infection.

5. The method of claim 4, wherein the bacterial infection is infection by *Haemophilus influenzae.*

6. The method of claim 1, further comprising administration of an antibiotic.

7. The method of claim 6, wherein the antibiotic is selected from the list consisting of amoxicillin, rifampicin, ciprofloxacin, azithromycin, clarithromycin, ceftriaxone, cefuroxime, and cefotaxime.

8. The method of claim 1, wherein the Arp2/3 inhibitor is an antibody that specifically binds to Arp2/3.

9. The method of claim 1, wherein the Arp2/3 inhibitor is administered together with a pharmaceutically acceptable carrier.

10. The method of claim 1, wherein the otitis media is selected from the group consisting of recurrent acute otitis media (RAOM), chronic otitis media with effusion (COME), acute post-tympanostomy otorrhea (APTO), and chronic suppurative otitis media (CSOM).

11. The method of claim 1, wherein the subject is human.

* * * * *